United States Patent [19]
Davies

[11] Patent Number: 4,606,085
[45] Date of Patent: Aug. 19, 1986

[54] HAND WASHING DEVICE

[76] Inventor: Joseph R. Davies, 220 W. Haven Ave., New Lenox, Ill. 60451

[21] Appl. No.: 716,538

[22] Filed: Mar. 27, 1985

[51] Int. Cl.⁴ .............................................. E03C 1/05
[52] U.S. Cl. .......................................... 4/623; 4/619; 4/624; 4/192; 4/DIG. 3
[58] Field of Search ................... 4/661, 619, 623, 192, 4/191, 605, 624, DIG. 3, 302, 304, 305, 628

[56] References Cited

U.S. PATENT DOCUMENTS

| | | | |
|---|---|---|---|
| 2,185,394 | 1/1940 | Arbogast | 4/DIG. 3 |
| 3,576,277 | 4/1971 | Blackmon | 4/623 |
| 3,639,920 | 2/1972 | Griffin et al. | 4/623 |
| 4,144,596 | 3/1979 | MacFarlane et al. | 4/DIG. 3 |
| 4,145,769 | 3/1979 | MacFarlane et al. | 4/DIG. 3 |
| 4,295,233 | 10/1981 | Hinkel et al. | 4/628 X |
| 4,335,619 | 6/1982 | Hinkel et al. | 4/628 X |
| 4,398,310 | 8/1983 | Lienhard | 4/623 |
| 4,402,095 | 9/1983 | Pepper | 4/623 |

Primary Examiner—Henry K. Artis
Attorney, Agent, or Firm—Charles F. Lind

[57] ABSTRACT

This invention relates to an electro mechanical-electronic device designed to prevent nosocomical contagions spread by the hands of health care personnel and others due to improper and incomplete hand washing. The device establishes a time reference for the personnel to insure the proper time standards of washing and rinsing hands are attained. Further, the automatic dispensing of a proper quantity of non-contaminated skin degermer and the replacement of natural emolients removed during the washing process is accomplished.

19 Claims, 4 Drawing Figures

Electrical Schematic

Equipment List

| | |
|---|---|
| 1 | Wash Basin |
| 2 | Faucet Set |
| 3 | Programmable Control Box |
| 4 | Flow Switch (normally open) |
| 5 | Line Fuse (120VAC) |
| 6 | Step-down Transformer (120-24VAC) |
| 7 | Voltage Switch |
| 8 | Programmable, two-cycle repeating timer (adjustable) |
| 9 | Wash Timer (timed open timer, adjustable) |
| 10 | Visual Indicator "Wash" Cycle |
| 11 | Soap Timer (timed open timer, adjustable) optional |
| 12 | Rinse Timer (timed open timer, adjustable) |
| 13 | Visual Indicator "Rinse" Cycle |
| 14 | Reset Timer (timed closed timer, adjustable) |
| 15 | Audible (Buzzer) Indicator |
| 16 | Imoluene Timer (timed closed timer, adjustable) optional |
| 17 | Translucent Tubing (disposable type) |
| 18 | Soap Pump (optional) |
| 19 | Imoluene Pump (optional) |
| 20 | Soap, Imoluene Dispenser (disposable type) |
| 21 | Air Seal (disposable type) |
| 22 | Personnel Detector (by customer) |
| 23 | Buzzer Timer (timed open timer, adjustable) |
| 24 | Master Relay |
| 8A | Nand Gate (Multiple) |

Figure 4

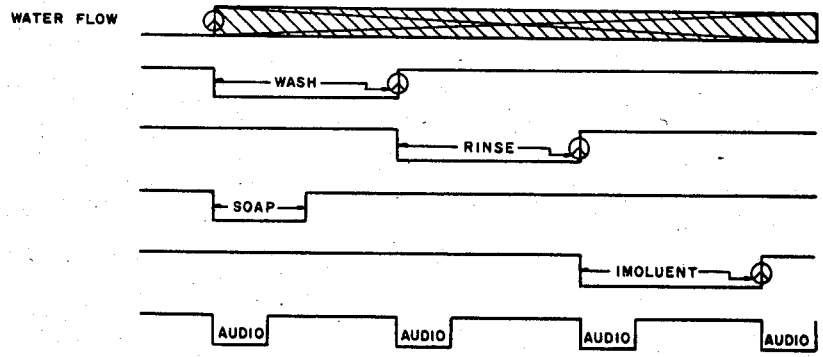

Programmable Time Sequence

HAND WASHING DEVICE

Despite the known importance of hand washing in the prevention of infection, hospital acquired infections of all types continue to plague U.S. hospitals. They are said to be linked to 100,000 deaths a year and affect an estimated 5 to 10% of the patients. The device described herein provides a means for health care personnel in both medical and public health fields to determine when they have met the time requirements for washing hands as recommended by the manufacturers of the anti-microbal soaps or liquids which they use and in turn have been approved by the U.S. Food & Drug Administration, as meeting standards for the control of infection. To start the hand washing time monitoring process, the device uses water flow detection initiated at the wash basin in anticipation of hand washing.

In most health care institutions the water is started by a foot pedal, knee pedal, or an elbow or wrist lever or electronic personnel detection. If this type of water control is not present, it is easily installed, thus eliminating any necessity for initiating water flow and starting the monitoring process with common contact points, such as push buttons, faucet handles, etc., which can result in cross infection.

The time monitoring device notifies the personnel both visually and auditorily of the duration of the proper wash cycle, (meaning the time used to apply the soap and lathering) which together with the rinse cycle represents the complete time for hand washing.

Currently, there are in the scrub rooms of hospitals where doctors and nurses prepare various types of timing devices, to advise personnel when they have met the time standards for scrubbing hands. However, in other areas of hospitals, health care institutions and offices, hand washing timing devices are not available and this critical time factor is largely left up to the discretion of the individuals. Recent research reveals where timing notification is lacking, the time involved in washing of hands by health care people does not meet the minimum standards recognized by national and international authorities.

The use of timing devices, such as are found in surgical scrub rooms would not be practical for hand washing in other areas of health care centers, hospitals and offices.

They are designed for people who scrub their hands a limited number of times a day. They use push buttons selecting time cycles and the users are required to concentrate on their scrubbing.

In other health care locations, the personnel often wash 50 to 100 times a day and are under stress to perform their designated duties and cannot direct their attenuation to hand washing. The units used in the surgical scrub rooms are bulky, comparatively expensive and not easily adapted to the many different types of hand washing facilities found in health care centers, whereas the device of this invention, can be installed rapidly and inexpensively on any type of hand washing fixture.

When health care personnel repeatedly wash their hands with a liquid soap or solution, containing a sufficient concentration of an anti-microbal agent to be a true germicide, as distinguished from an inhibitor of growth, they find their hands often become dry, chapped, and cracked. To overcome this problem some manufacturers of skin degerming products have marketed a lotion soap, which contains a substantial percentage of non functional additives or emolients, but, only a sufficicient quantity of an anti-microbal agent to act as an inhibitor to their growth. Although, these lotion products alleviate the problem of dermatotic hands, their use is limited to the less critical areas of hospitals and health care institutions, where cross infection is not as prevelant.

With the use of the device described herein the anti-microbal agent of the skin degermer can be used at a strength which is a true germacide for a proper duration, so that there are no limitations as to the locations where it is used. Any residue from the rubbing and lathering are promptly removed with the start of the rinse cycle minimizing the effect of the harsh germacide on the skin. This is in contrast to and unlike the lotion soaps where the residue is often used without water and left on the hands. Additionally, research has shown that rubbing the hands vigorously in plain water, as is done in rinsing, has an anti-bacterial effect even without antiseptic preparations. Further, studies show some effective germacides can be absorbed thru the skin with harmful results, offering yet another reason for prompt and complete removal of residue by the rinse cycle. Thus many of the existing problems of health care hand washing can be overcome when the device of this invention is present.

With this device there is a means of automatically dispensing an uncontaminated skin degerming product, at the start of hand washing and any desired additive at the end.

Another feature is that in teaching hospitals or other health care institutions, where supervisory personnel at remote locations wish to monitor time compliance with designated hand washing procedures, this can be readily accomplished by simply wiring in a remote location with the control panel near the wash basin and using mirrors to identify personnel involved, when a electronic personnel detector shows they have left the vicinity of the wash basin prior to completion of hand washing procedure.

SUMMARY OF THE INVENTION

One of the objects of this invention, is to provide health care personnel and others with a means of recognizing via a visible and/or audible notice when they have completed a prescribed time cycle for washing hands, there being one for applying soap and working up the lather and one for rinsing hands.

The second object of this invention, is to provide health care personnel with a system, as described in the preceding object, which is automatic, in that it does not require personnel to perform any additional functions, other than the ones to which they are accustomed, when washing and rinsing hands.

The third object of this invention, is to design the electro mechanical-electronic circuit that even though the time elements are initiated by the flow of water, any temporary interruptions due to personal habits of shutting off the water, and turning it on again during hand washing, will not affect the duration of the time cycles.

The fourth object of this invention, is to have the device for hand washing and rinsing as described in the preceding objects, to be: activated and terminated without contact by fingers or hands, easily maintained, relatively inexpensive, and readily adaptable to a wide variety of existing hand washing facilities.

The fifth object of the invention, is to provide a hand washing aid, with programable time elements, so that each segment of the procedure can be performed at a time and with a duration that research shows will result in maximum benefits for disease control, with a minimum of determental factors.

The sixth object of this invention, is to provide a means, at the beginning of hand washing, for automatically dispensing near the basin, uncontaminated skin degerming products in a proper quantity, and which use disposable containers for storage, and disposable media to transfer the degerming product to the wash basin from the storage container.

The seventh object of this invention, is to provide a means at the end of the rinse cycle to dispense automatically near the basin, any desired uncontaminated additives which can be used to neutralize undesirable residue left on the hands at the end of the washing procedures, or to replace oils or emolients those removed from the skin during hand washing, thus minimizing the problem of dermatatic hands common with frequent hand washing.

The eighth object of this invention is to provide a means whereby any liquid degerming product and/or additive used in hand washing can be kept air sealed when not being dispensed.

BRIEF DESCRIPTION OF DRAWINGS

FIG. 4 is an equipment list showing the numbers assigned to the various components.

FIG. 5 illustrates one of the possible time sequences of hand washing cycle.

OPERATION & DESCRIPTION OF THE INVENTION

Figure 1:
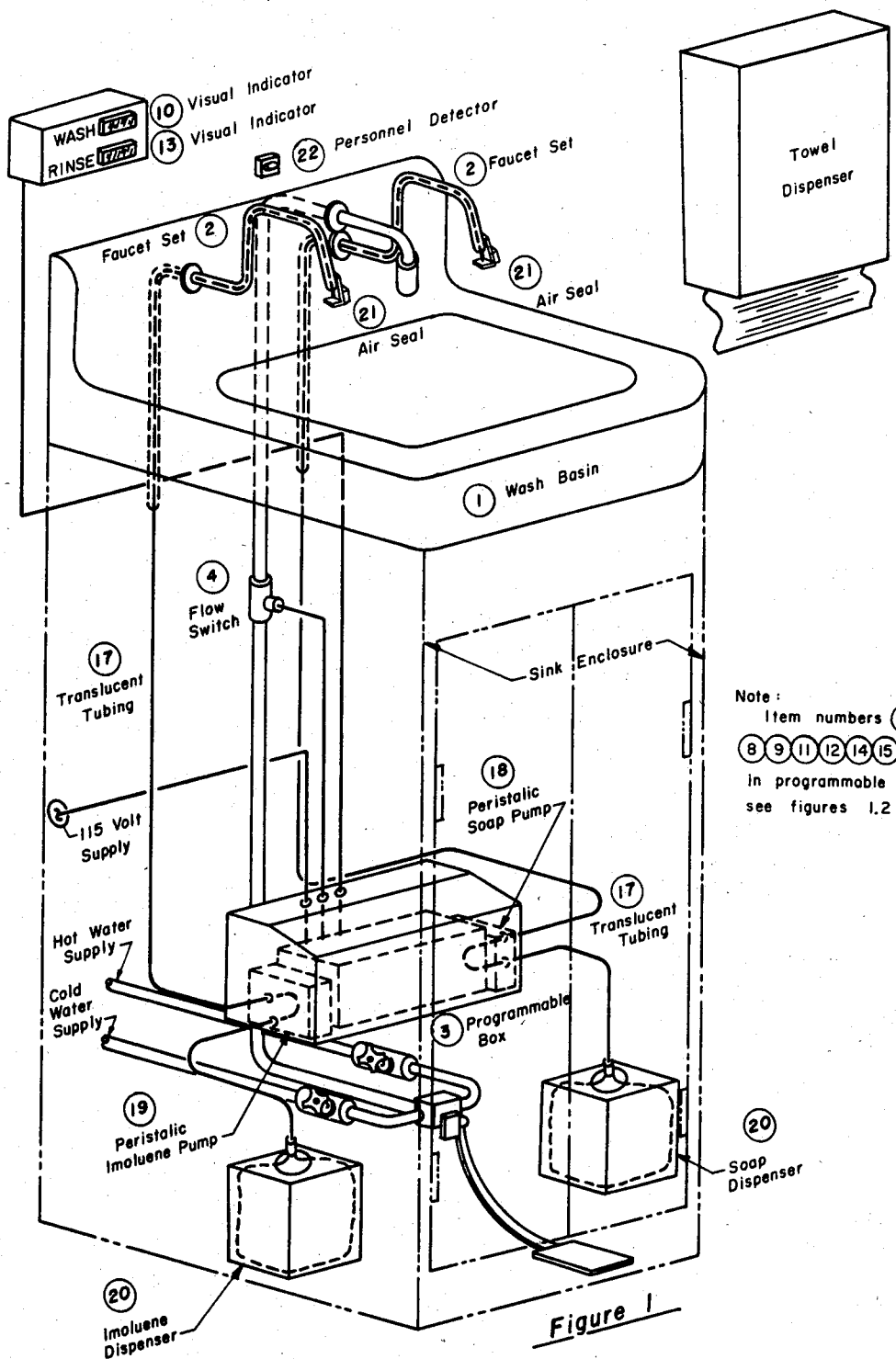
FIG. 1 is a perspective view of the device showing the various components.
Figure 3:
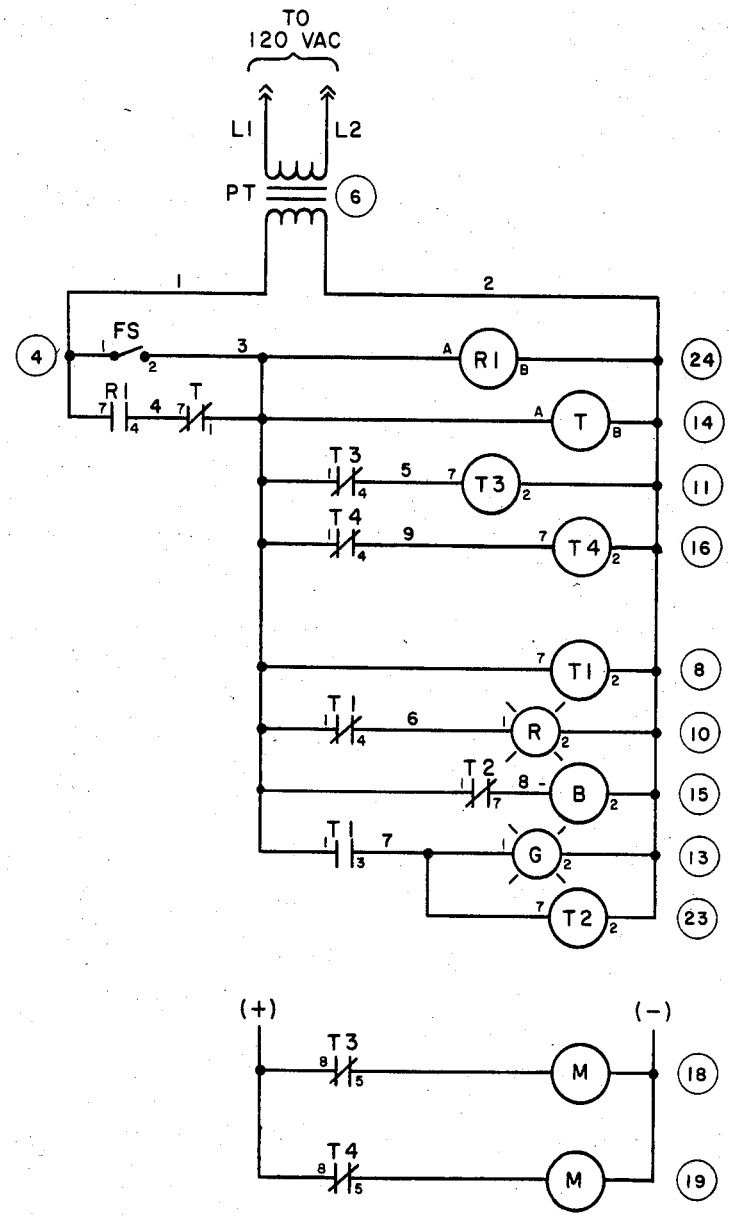
FIG. 3 is a schematic drawing of an electro mechanical circuit.

As is illustrated in FIG. 1, the water is premixed from hot water supply lines, which are controlled by means of a foot pedal. The premixed water is fed through a flow switch 4, on its way to the wash basin 1. In the event the water was not premixed, the flow switch would be installed on the hot water line, which is customarily turned on first in hand washing. With the flow of water, the normally open contacts FS-1 and FS-2 (see FIG. 3) of flow switch 4 close which energizes the entire circuitry, drawing power from an external source in the building, via the lines L1 & L2, as shown in FIG. 3. These lines are connected to step down transformer 6, to reduce the 120 Volts A.C. to 24 Volts A.C., to provide a safe voltage of 24 Volt A.C. potential through lines L1 & L2.

Figure 2:
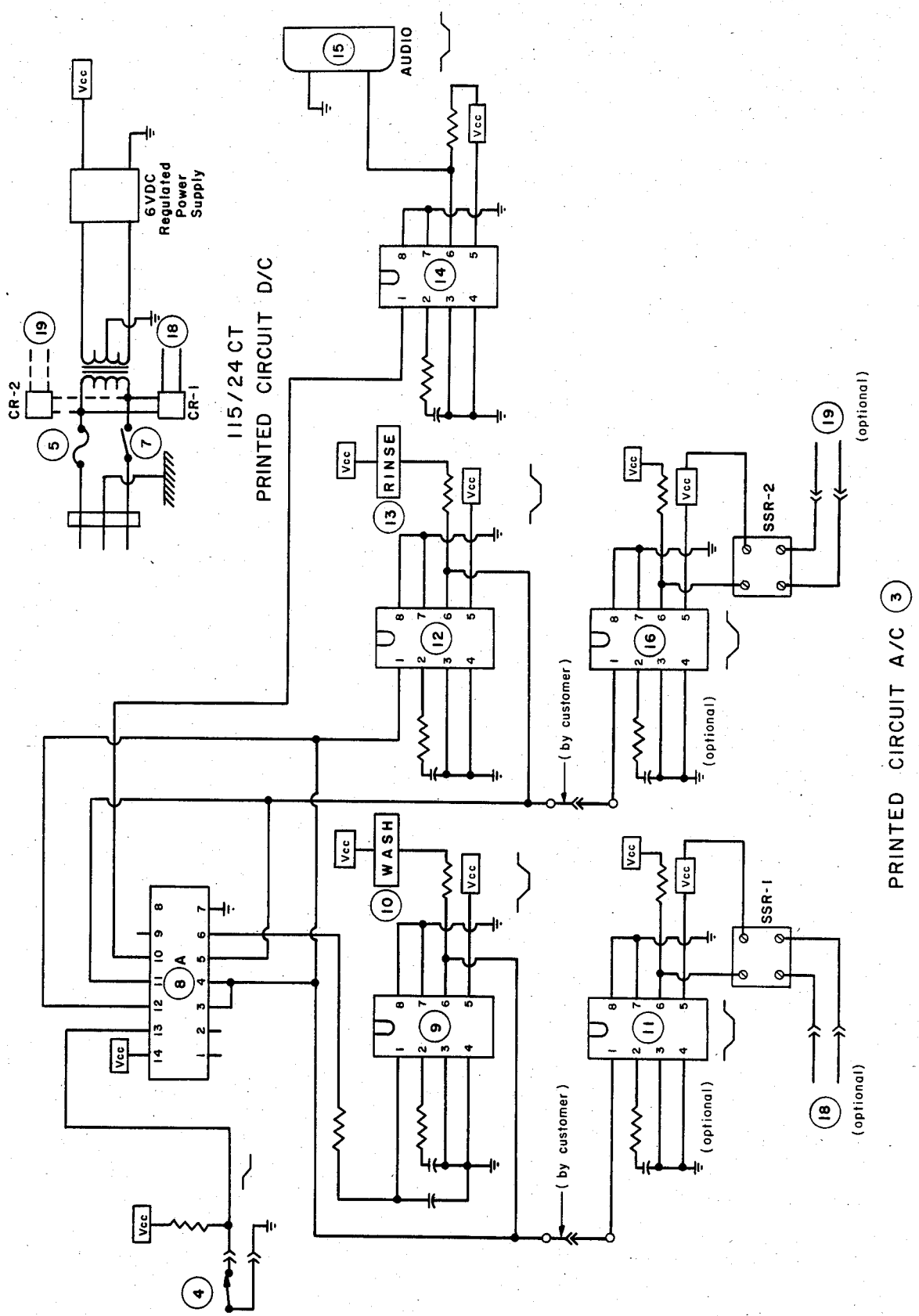
FIG. 2 is an illustration of an optional electronic circuitry using a printed circuit.

The circuitry remains de-energized until the closing of flow switch 4, whereupon the following sequence of events then takes place. The timing of the sequence is controlled by components of programable control box 3, as are illustrated in FIG. 2. Relay R1 is energized and closes the normally open contacts R1-4 & R1-7, latching control power onto the circuitry. The circuit is now independent of the action of the flow switch 4, and will complete the programed time cycles, independent of water flow. Reset timer T is energized and contacts T7 & T1 are set and will so remain until the end of the complete hand washing procedure.

Wash and rinse cycle timer T1 (See FIG. 3) is a dual cycle timer that is also then simultaneously energized. The first cycle closes contacts T1-1 & T1-4 providing power to the wash lamp 10 which is now illuminated, giving visual notice that the wash cycle has begun.

Likewise, the first cycle of recycling buzzer Timer T2 is energized, closing contacts T2-1 & T2-7, supplying power to buzzer 15, located in the control box 3, giving audible notice of the start of the wash cycle. Simultaneously with the energizing of the circuitry, the energized soap dispenser timer T3 closes normally open contacts T3-1 & T3-4, releasing 120 Volts A.C. power direct to the soap pump motor 18, by closing normally open contacts T3-8 & T3-5. Since a plug in transformer with low amperage can be used for power for all components except peristalic pumps 18 & 19, power for these pumps is supplied separately, as not every user will want soap and emolient dispensers.

After a short interval, the first cycle of timer T2 times out and changes state, opening contacts T2-1 & T2-7, whereupon the buzzer stops. After a proper amount of soap has been dispensed, timer T3 times out and reopens contacts T3-1 & T3-4, whereupon contacts T3-8 & T3-5 open, stopping the pump.

The first time cycle of T1 is completed after a proper programed wash time, and the contacts T1-1 & T1-4 open, and remove power from wash lamp 10, which is now extinguished. The second time cycle of timer T1 starts and the contacts T1-1 & T1-3 now close, supplying power to rinse lamp 13 which is now lighted. Buzzer timer T2 at this point starts to recycle, again closing contacts T2-1 & T2-7 supplying control power to sound the buzzer 15, for a short time, after which it changes state and again opens contacts T2-1 & T2-7. At the end of the second time cycle of timer T1, contacts T1-1 & T1-3 now open, removing power from the visual rinse indicator 13. Buzzer timer T2 starts to recycle for a third time closing contacts T2-1 & T2-7, again supplying power to the buzzer for a short period before they reopen giving audible notice of completion of the hand washing.

Emolient timer T4, whose contacts T4-1 & T4-4 have been programed to remain open from the time the circuit was energized, now change state and close, releasing 120 Volts A.C. direct to the emolient pump, by closing normally open contacts T4-8 & T4-5. After a proper amount of emolient has been dispensed and the timer T4 times out, contacts T4-1 & T4-7 and contacts T4-8 & T4-5 reopen, stopping the pump.

Since the hand washing procedure is now complete, reset timer times out opening normally open contacts T1 & T7 7, thus removing all power from the circuitry, preparing the same for the next operation, which again, will be started with the flow of the water to the wash basin, in anticipation of hand washing.

The timing of the various parts of the hand washing procedure, described herein before, makes use of dual cycle timers, where possible, in an effort to save space and expense. However, this is not meant to limit the design when it is desirable to use two single timers, that can be programed independentaly of each other; instead of using a repeating cycle.

With the start of the motor on soap pump 18, controlled by timer T3, the peristalic pump 18 draws soap from the throw away sealed plastic bag in cardboard box 20, through throw away flexible translucent tubing 17 and, pumps it upward through the tubing. The tubing is encased in a semi-rigid metal casing, in the vicinity of wash basin 1, thereby holding the tubing 17 in place so that it discharges through the righthand faucet set fixture 2 into the wash basin. The end of this fixture is capped by a throw away spring activated self-closing air seal, which is normally closed, except when fluid pressure is applied by the liquid soap being pumped from pump 18.

As previously mentioned, nothing touches the soap from the time it leaves the sealed container 20 until it is discharged in the wash basin. The entire translucent tubing 17 can be removed in a matter of minutes, by unscrewing two screws that hold the tubing 17 in place over the rollers of the peristalic pump 18, and then replacing the tubing by threading it back through the same channels from which it was removed.

Timing and delivery of a proper quantity of emolient to the lefthand side of the basin through lefthand fixture of the faucet set 2, as previously described is controlled by timer T4. The method of delivery is the same as used for liquid soap on the righthand side of the wash basin 1.

In the electronic printed circuit system, described hereinafter and illustrated in FIG. 2, a outside power sourse in the building is used to provide operating potential for a regulated D.C. power supply. The power supply provides line power isolation and is fused for protection against catastrophic failure.

The closing contacts of the water flow switch 4 causes one input of the NAND gate 8A to go low. The condition of all inputs being high is no longer satisfied, causing the outputs of the NAND gate to go to a high state. The output of the NAND gate 8A is tied to the input of the wash timer 9 which is triggered by the transition from the low to the high state. A second input to the NAND gate 8-A is tied to the output of the wash timer 9. The wash timer 9 output goes to a low state for the timed wash cycle. In respect to the NAND gate 8A, if anyone of the three inputs or some combination of the same are low, the output of the NAND gate will remain high. If either wash timer 9 or rinse timer 12 is timing, no input from the flow switch 4 is possible.

When triggered, the wash timer 9 powers the wash lamp 10 and illuminates it. At the low to high transition of the NAND gate 8A, the soap dispenser timer 11 is triggered. The output of the soap dispenser timer 11 is tied to a solid state relay SSR-1, to effect electrically isolated and electrically noiseless control of any power levels used for the soap dispenser pump 18. After the time interval needed to dispense the appropriate amount of soap, the timer 11 times out and removes the power from the pump 18. The second NAND gate (part of 8A) is used to monitor the status of the flow switch 4, the wash cycle timer 9, and the rinse cycle timer 12. The three inputs of the NAND gate 8A are coupled to outputs of the before mentioned devices. Should anyone of the three change state from high to low, the output of the NAND gate 8A will go from low to high, triggering the buzzer timer 14 and causing a short audible notice at the beginning of the wash and rinse cycles and at the end of the rinse cycle. At the end of the wash cycle, the output of the wash cycle timer 9 changes from low to high, triggering the rinse cycle timer 12. The wash lamp 10 is extinguished and the rinse lamp 13 is illuminated at the start and remains illuminated until the end of the rinse cycle; whereupon the rinse lamp 13 is extinguished, and the emolient timer 16 is triggered. The emolient timer 16 also has a solid state relay SSR-2 off the output of the timer that controls power supplied to the emolient pump 19. After a sufficient time to provide a proper amount of emolient, the timer 16 times out and removes the power from the emolient pump 19. This circuit is so designed that when the hand washing procedure has reached the end of the rinse cycle, another individual can start to wash without disturbing the dispensing of emolient to the individual who has just finished.

When desired for control purposes, with the use of a modified infrared personnel detector mounted just above the wash basin, anyone leaving the wash basin, prior to completion of the hand washing procedure, can easily be identified through a visual and/or audible notice.

It should be noted that both the electro mechanical and the electronic systems will complete their programed wash and rinse cycles, independent of how many times the water flow to the basin is interrupted. Research has shown that hospital workers or personnel are not likely to change long standing habits, such as shuting off the water at any time to conserve usage, and/or restarting the same later, or discontinuing water use temporarily to adjust water temperature, etc.

What is claimed is:

1. For use by health care personnel and others in washing their hands with water and a cleanser, the improved combination comprising:

a sealed source of the cleanser, and means to pump the cleanser, while yet sealed, from the source for discharge onto the person's hands;

a number of indicators;

valve means activated by such personnel when individually ready to begin washing by manual body action other than below the wrist, operable to start and stop water flow for discharge onto the person's hands, timer means;

means activated upon the water beginning to flow, operable to activate the timer means and initiate the wash cycle;

said timer means being operable upon the water flow starting, to:

remain operating independently of the subsequent condition of the valve means and the continued or discontinued flow of water;

activate the cleanser pump means, for a short timed duration, for discharging the cleanser onto the person's hands, and;

activate one of the indicators, for an extended timed duration corresponding to the washing phase of the wash cycle, for advising the person that the wash cycle is in the washing phase;

said timer means being operable sequentially after the timed washing phase of the wash cycle, to:

activate another of the indicators, for an extended timed duration corresponding to the rinsing phase of the wash cycle, for advising the person that the wash cycle is in the rinsing phase;

said timer means being operable at the start of the timed washing phase of the wash cycle, at the start of the timed rinsing phase of the wash cycle, and at the end of the timed rinsing phase of the wash cycle, to:

activate yet a third of the indicators, for a short duration compared to the duration of the corresponding wash or rinse phases of the wash cycle, to advise the person that the changes in the timed phases should then be taking place;

operable thereby to advise a person washing his/her hands what phase of the overall wash cycle, the washing or rinsing, the person should be in to satisfy the corresponding duration needed to be effective for proper degermification.

2. A combination according to claim 1, wherein the one and the other indicators, for advising of the washing and rinsing phases of the wash cycle, are visual, and wherein the third indicator, for advising that the various phases of the wash cycle are starting/ending, is audio.

3. A combination according to claim 1, wherein the cleanser is sealed in a throw-away flexible container, wherein a flexible tube extends from the container to an outlet from which the cleanser is discharged onto the person's hands, and wherein a peristalic pump cooperates with the tube to serve as the means for pumping the cleanser while yet sealed from the container and onto the person's hands.

4. A combination according to claim 3, wherein the one and the other indicators, for advising of the washing and rinsing phases of the wash cycle, are visual, and wherein the third indicator, for advising that the various phases of the wash cycle are starting/ending, is audio.

5. For use by health care personnel and others in washing their hands with water and a cleanser, and for post-treating the hands with an embolient, the improved combination comprising:

a sealed source of the cleanser, and means to pump the cleanser, while yet sealed, from the source for discharge onto the person's hands;

a sealed source of the post-washing emolient, and means to pump the emolient, while yet sealed from the source for discharge onto the person's hands;

a number of indicators;

valve means activated by such personnel when individually ready to begin washing, by manual body action other than below the wrist, operable to start and stop water flow through a water line for discharge onto the person's hands, timer means;

means activated upon the water beginning to flow, operable to activate the timer means and initiate the wash cycle;

said timer means being operable upon the water flow starting, to:

remain operating independently of the subsequent condition of the valve means and the continued or discontinued flow of water;

activate the cleanser pump means, for a short timed duration, for discharging the sealed cleanser onto the person's hands, and;

activate one of the indicators, for an extended timed duration corresponding to the washing phase of the wash cycle, for advising the person that the wash cycle is in the washing phase;

said timer means being operable sequentially after the timed washing phase of the wash cycle; to:

activate another of the indicators, for an extended timed duration corresponding to the rinsing phase of the wash cycle, for advising the person that the wash cycle is in the rinsing phase;

said timer means being operable sequentially after the timed rinsing phase of the wash cycle, to:

activate the emolient pump means, for a short timed duration corresponding to the post-treating phase of the wash cycle, where the sealed emolient may be discharged onto the person's hands;

said timer means being operable at the start of the timed washing phase of the wash cycle, at the start of the timed rinsing phase of the wash cycle, at the end of the timed rinsing phase of the wash cycle, and at the end of the timed emolient discharge post-treating phase of the wash cycle, in timed sequences, to:

activate yet a third of the indicators, for a short duration compared to the duration of the corresponding washing, rinsing or post-treating phases of the wash cycle, to advise the person that the changes in the timed phases should then be taking place;

operable thereby to advise a person washing his/her hands what phase of the overall wash cycle, the washing, rinsing, or post-treating phase, the person should be in to satisfy the corresponding duration needed to be effective for proper degermification.

6. A combination according to claim 5, wherein the one and the other indicators, for advising of the washing and rinsing phases of the wash cycle, are visual, and wherein the third indicator, for advising that the various phases of the wash cycle are starting/ending, is audible.

7. A combination according to claim 5, wherein the emolient is sealed in a throw-away flexible container, wherein a flexible tube extends from the container to an outlet from which the emolient is discharged onto the person's hands, and wherein a peristalic pump cooperates with the tube to serve as the means for pumping the emolient while yet sealed from the container and onto the person's hands.

8. A timer combination according to claim 5, wherein the cleanser is sealed in a container, wherein a flexible tube extends from the container to an outlet from which the cleanser is discharged onto the person's hands, wherein a peristalic pump cooperates with the tube to serve as the means for pumping the cleanser from the container and onto the person's hands;

wherein the emolient is sealed in a container, wherein a flexible tube extends from the container to an outlet from which the emolient is discharged onto the person's hands, and wherein a peristalic pump cooperates with the tube to serve as the means for pumping the emolient from the container and onto the person's hands.

9. A timer combination according to claim 5, wherein the cleanser is sealed in a throw-away flexible container, wherein a flexible tube extends from the container to an outlet from which the sealed cleanser is discharged onto the person's hands, wherein a peristalic pump cooperates with the tube to serve as the means for pumping the cleanser while yet sealed from the container and onto the person's hands;

wherein the emolient is sealed in a throw-away flexible container, wherein a flexible tube extends from the container to an outlet from which the sealed emolient is discharged onto the person's hands, and wherein a peristalic pump cooperates with the tube to serve as the means for pumping the emolient while yet sealed from the container and onto the person's hands.

10. A combination according to claim 1, wherein the valve means is foot activated by such personnel.

11. A combination according to claim 1, wherein the means activated upon the water beginning to flow is in the form of a flow switch in the water line, the flow switch being operable to activate the timer means and initiate the wash cycle.

12. A combination according to claim 3, wherein further a spring activated self-closing air seal is located across the outlet for the cleanser, the seal normally being closed and being opened only when the cleanser is actually being pumped from the outlet and onto the person's hands.

13. A combination according to claim 12, wherein the means activated upon the water beginning to flow is in the form of a flow switch in the water line, the flow switch being operable to activate the timer means and initiate the wash cycle.

14. A combination according to claim 5, wherein the means activated upon the water beginning to flow is in the form of a flow switch in the water line, the flow switch being operable to activate the timer means and initiate the wash cycle.

15. A combination according to claim 7, wherein further a spring activated self-closing air seal is located across the outlet for the emolient, the seal normally being closed and being opened only when the emolient is actually being pumped from the outlet and onto the person's hands.

16. A combination according to claim 8, wherein further a spring activated self-closing air seal is located across each outlet, respectively for the cleanser and for the emolient, the seal normally being closed and being opened only when the respective cleanser or emolient is actually being pumped from the outlet and onto the person's hands.

17. A combination according to claim 16, wherein the means activated upon the water beginning to flow is in the form of a flow switch in the water line, the flow switch being operable to activate the timer means and initiate the wash cycle.

18. For use by health care personnel and others in washing their hands at a wash basin with water and a cleanser, the improved combination comprising:

a sealed throw-away flexible container holding cleanser, a flexible tube extending from the container to an outlet at the wash basin from which the cleanser is discharged onto the person's hands, a spring activated self-closing air seal located across and normally closing the outlet, and a peristalic pump cooperating with the tube to serve as the means for pumping the cleanser via the outlet from the container and onto the person's hands;

valve means manually activated by such personnel when individually ready to begin washing, operable to start and stop water flow through a water line for discharge onto the person's hands, an audible indicator;

timer means;

means activated upon the water beginning to flow, operable to activate the timer means and initiate the wash cycle;

said timer means being operable upon the water flow starting, to remain operating independently of the subsequent continued or discontinued flow of water;

said timer means also being operable to activate the cleanser pump, for a short timed duration, for discharging the sealed cleanser onto the person's hands at the start of a timed washing phase of the wash cycle;

said timer means also being operable, at three separate and sequential intervals corresponding to the start of the timed washing phase of the wash cycle, and at the start and at the end of a timed rinsing phase of the wash cycle, to activate the audible indicator, said timer means activating the audible indicator, for only a short duration compared to the duration of the corresponding washing and rinsing phases of the wash cycle, operable thereby to advise a person washing his/her hands what phase of the overall wash cycle, the washing or rinsing, the person should be in to satisfy the corresponding duration needed to be effective for proper degermification.

19. A combination according to claim 18, further including a sealed throw-away flexible container holding emolient, a flexible tube extending from the container to an outlet at the wash basin from which the emolient is discharged onto the person's hands, a spring activated self-closing air seal located across and normally closing the outlet, and a peristalic pump cooperating with the tube to serve as the means for pumping the emolient while yet sealed from the container and onto the person's hands; and said timer means also being operable sequentially after the timed rinsing phase of the wash cycle, to activate the emolient pump, for a short timed duration corresponding to a post-treating phase of the wash cycle, where the sealed emolient may be discharged onto the person's hands.

* * * * *